United States Patent [19]

White et al.

[11] 4,360,519

[45] Nov. 23, 1982

[54] ANALGESIC METHOD USING A MORPHOLINE COMPOUND

[75] Inventors: Alan C. White, Windsor; Edwin T. Edington, Cookham, both of England

[73] Assignee: John Wyeth & Brother Limited, Maidenhead, England

[21] Appl. No.: 193,779

[22] Filed: Oct. 3, 1980

[30] Foreign Application Priority Data

Oct. 20, 1979 [GB] United Kingdom ............... 7936502

[51] Int. Cl.$^3$ ............................................. A61K 31/535
[52] U.S. Cl. ........................ 424/248.55; 424/248.58; 544/171; 544/173; 544/174; 544/152
[58] Field of Search ............... 544/171, 173, 174, 152; 424/248.55, 248.58

[56] References Cited

U.S. PATENT DOCUMENTS 2,997,469  8/1961  Heel et al. ........................ 544/173
3,112,311  11/1963  Zimmermann et al. ............ 544/173
3,296,076  1/1967  Thomä ............................. 544/173

FOREIGN PATENT DOCUMENTS 773780  5/1957  United Kingdom .
791416  3/1958  United Kingdom .
862198  3/1961  United Kingdom .

Primary Examiner—Robert W. Ramsuer
Attorney, Agent, or Firm—Arthur G. Seifert

[57] ABSTRACT

Morpholine derivatives of the formula

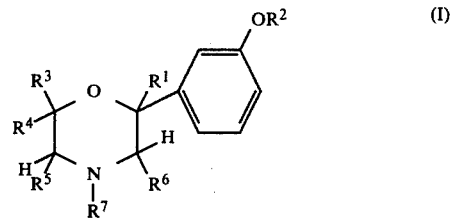

and their pharmaceutically acceptable acid addition salts[wherein $R^1$ represents lower alkyl. $R^2$ represents hydrogen, lower alkyl, benzyl, lower alkoxymethyl or an acyl group; $R^3$ represents hydrogen, lower alkyl or phenyl; $R^4$, $R^5$ and $R^6$ are independently hydrogen or lower alkyl and $R^7$ is hydrogen, lower alkyl, lower alkenyl, lower alkynyl, aryl(lower)alkyl, tetrahydrofurylmethyl or cycloalkylmethyl] possess analgesic and/or opiate antagonistic activity.

1 Claim, No Drawings

ANALGESIC METHOD USING A MORPHOLINE COMPOUND

This invention relates to morpholine derivatives, to processes for their preparation and to pharmaceutical compositions containing them.

The present invention provides novel morpholine derivatives of the general formula (I)

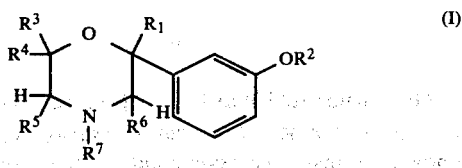

and their pharmaceutically acceptable acid addition salts. In this formula $R^1$ represents lower alkyl; $R^2$ represents hydrogen, lower alkyl, benzyl, (lower)alkoxymethyl or an acyl group; $R^3$ represents hydrogen, lower alkyl or phenyl; $R^4$, $R^5$ and $R^6$ are independently hydrogen or lower alkyl and $R^7$ is hydrogen, lower alkyl, lower alkenyl, lower alkynyl, aryl(lower)alkyl, 2-tetrahydrofurylmethyl or cycloalkylmethyl.

The term "lower" as used herein means that the radical referred to contains 1 to 6 carbon atoms. The radical preferably contains 1 to 4 carbon atoms. For example when any of the groups $R^1$, $R^2$, $R^3$, $R^4$, $R^5$, $R^6$ and $R^7$ is a lower alkyl group the radical may be, for example, methyl, ethyl, propyl or butyl. When $R^7$ is lower alkenyl or lower alkynyl suitable groups include, for example allyl, 2-methyl-2-propenyl, 3-methylbut-2-enyl and propynyl. When $R^7$ is cycloalkylmethyl the group is preferably cyclopropylmethyl or cyclobutylmethyl. When $R^7$ is aryl(lower)alkyl the group can be, for example benzyl or phenethyl. When $R^2$ is an acyl group it is preferably a lower alkanoyl group such as acetyl, propionyl or butyryl. When $R^2$ is a (lower)alkoxymethyl group it is preferably a methoxymethyl group.

In a preferred group of compounds of general formula I, $R^1$ is an ethyl group, $R^2$ is hydrogen, $R^3$ is hydrogen or lower alkyl (e.g. methyl), $R^4$, $R^5$ and $R^6$ are hydrogen and $R^7$ is lower alkyl (e.g. methyl).

The compounds of the invention can be prepared by reduction of a compound of general formula (II)

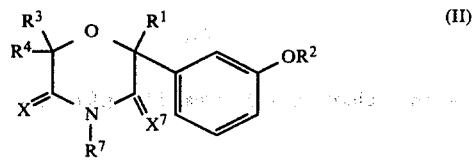

wherein $R^1$, $R^2$, $R^3$, $R^4$ and $R^7$ are as defined above, X is oxo or

/R$^5$
\H (where $R^5$ is as defined above) and $X^1$ is oxo or

/R$^6$
\H (where $R^6$ is as defined above) with the proviso that at least one of X and $X^1$ is oxo and if desired converting a free base of general formula (I) into a pharmaceutically acceptable acid addition salt thereof. The compound of general formula (II) can be reduced with, for example, a hydride transfer agent (e.g. lithium aluminium hydride).

Once a compound of general formula (I) has been prepared it may be converted into another compound of general formula (I) by methods known per se. For example, a compound in which $R^7$ is lower alkyl, lower alkenyl, lower alkynyl, aryl(lower)alkyl, 2-tetrahydrofurylmethyl or cycloalkylmethyl may be prepared by "N-alkylating" a compound in which $R^7$ is hydrogen. By "N-alkylating" is meant introducing on to the nitrogen atom of the morpholine ring a lower alkyl, lower alkenyl, lower alkynyl, aryl(lower)alkyl,2-tetrahydrofurylmethyl or cycloalkylmethyl radical. In one method of carrying out the "N-alkylating" process a compound of general formula I in which $R^7$ is hydrogen is reacted with a halide of general formula $R^{7'}$—Hal where $R^{7'}$ is lower alkyl, lower alkenyl, lower alkynyl, aryl(lower)alkyl, 2-tetrahydrofurylmethyl or cycloalkylmethyl in the presence of an acid acceptor such as an alkali metal carbonate (e.g. potassium carbonate), preferably in solution in an organic solvent.

Alternatively the compound of general formula (I) in which $R^7$ is hydrogen may be alkylated by reductive alkylation i.e. by treatment with an aldehyde and hydrogen in presence of a hydrogenation catalyst. A preferred method of cycloalkyl-methylating involves reacting the N-unsubstituted compound with a cycloalkylcarbonyl chloride to give an intermediate N-carbonyl cycloalkyl compound which may be reduced with, for example, a hydride transfer agent.

A compound of general formula (I) in which $R^2$ is a hydrogen atom can be obtained from a corresponding compound in which $R^2$ is lower alkyl, lower alkoxymethyl or benzyl by splitting off the ether group in known manner, e.g. by treating the lower alkyl or benzyl ether with hydrogen bromide or boron tribromide, by treating the lower alkyl ether with diisobutylaluminium hydride or by subjecting the benzyl ether to hydrogenolysis or by treating the (lower)alkoxymethyl ether with dilute acid. Similarly a compound of general formula (I) in which $R^7$ is benzyl may be hydrogenolysed to a compound of general formula (I) in which $R^7$ is hydrogen which, if desired may then be "alkylated" as hereinbefore described. Compounds in which $R^7$ is lower alkyl, particularly methyl may also be dealkylated to compounds in which $R^7$ is hydrogen, e.g. by reaction with ethyl-,phenyl-,vinyl- or 2,2,2-trichloroethyl-chloroformate followed by removal of the resulting N-substituent with, for example, dilute acid or zinc and acetic acid or basic conditions as appropriate.

A compound of general formula (I) in which $R^2$ is hydrogen can be acylated (e.g. with acetic anhydride)

to give a corresponding compound in which $R^2$ is an acyl group such as a lower alkanoyl radical.

Two or more of the above mentioned processes for interconverting the compounds of general formula (I) may, if desired, be carried out consecutively. In some instances it may be necessary to protect one or more of the functional groups on the molecule while reaction occurs at another functional group and then subsequently remove the protecting group or groups.

The preferred compound of general formula (II) is one in which X represents oxo and $X^1$ represents

This compound may be prepared by cyclisation of a haloamide of general formula (III)

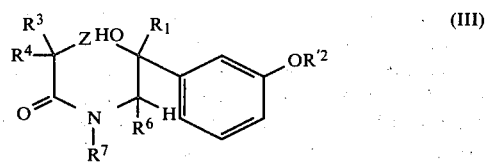

(III)

wherein $R^1$, $R^3$, $R^4$, $R^6$ and $R^7$ are as defined above, $R^{2'}$ is lower alkyl, (lower)alkoxymethyl or benzyl, and Z is bromo or chloro. If desired the $R^2$ group [lower alkyl, (lower)alkoxymethyl or benzyl] in the resulting amide of general formula (II) may be converted into another $R^2$ group (hydrogen or acyl) by selection of a suitable method from the methods described above in connection with the interconversion of the $R^2$ group in compound I. Again, if desired, an amide of formula (II) where $R^4$ is hydrogen may be alkylated to give an amide where $R^4$ is lower alkyl e.g. by reaction with a lower alkyl halide to presence of a strong base. Examples of strong bases are given hereinbelow.

The cyclisation of the haloamide of general formula (III) may be carried out with a basic agent such as an alkali metal hydride or alkali metal hydroxide. The haloamide is preferably prepared by condensing an α-halo acid halide of general formula (IV)

(IV)

where $R^3$, $R^4$, and Z are as defined above and $Z^1$ is chloro or bromo with an aminoalcohol of general formula (V)

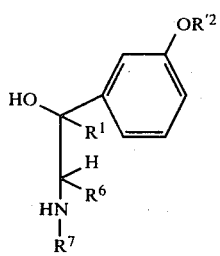

(V)

where $R^1$, $R^{2'}$, $R^6$ and $R^7$ are as defined above. The condensation can be carried out in presence of a basic condensing agent, e.g. triethylamine. It is not necessary to purify the haloamide (III) from the reaction mixture; the crude compound can be cyclised directly to the compound (II) where X is oxo and $X^1$ is

The α-halo acid halide (IV) and the aminoalcohol (V) are known compounds or can be prepared by methods known for analogous compounds. A preferred method for preparing the aminoalcohol (V) involves reaction of an oxiran of general formula (VI)

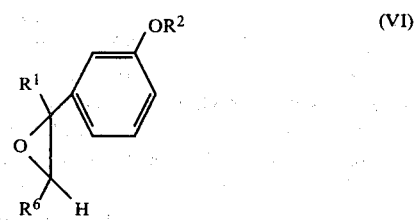

(VI)

with an amine of general formula

$R^7$—$NH_2$ (VII)

The amides of general formula (II) in which $X^1$ represents oxo and X is

may be prepared in an analogous manner to that described above for amides in which X represents oxo and $X^1$ is

e.g. by cyclisation of a haloamide of formula

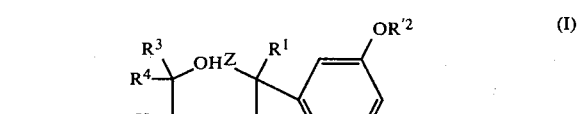

(I)

(where $R^1$, $R^{2'}$, $R^3$, $R^4$, $R^5$, $R^7$ and Z are as defined above). Alternatively a compound of general formula (VIII)

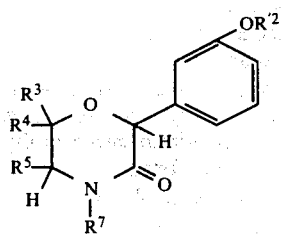 (VIII)

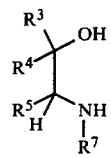 (X)

or by reacting an oxiran of general formula

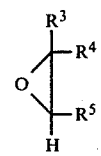

with a hydroxyamine of general formula

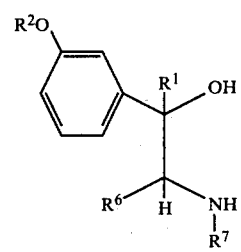

where $R^1$, $R^2$, $R^3$, $R^4$, $R^5$, $R^6$ and $R^7$ are as defined above.

(where $R^{2'}$, $R^3$, $R^4$, $R^5$ and $R^7$ are as defined above) may be alkylated (e.g. with a lower alkyl halide in presence of a strong base such as sodamide, lithium diisopropylamide lithium tetramethylpiperidide, bromomagnesium diisopropylamide or N-tertiarybutylcyclohexylamide) to give the desired amide of general formula (II). The compound of general formula (VIII) may be prepared in an analogous manner to that described above for the preparation of the amide of general formula (II) in which X is oxo e.g. by condensation of an appropriate α-halo acid halide with an appropriate aminoalcohol. The compounds of formula (II) in which X and $X^1$ are both oxo may be prepared by reacting a dicarboxylic acid of general formula

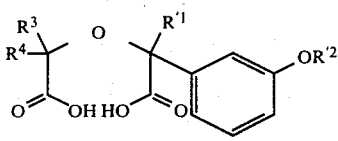

where $R^{2'}$, $R^3$ and $R^4$ are as defined above and $R^{1'}$ is hydrogen or lower alkyl with ammonia or with an amine of formula $NH_2R^7$ and where $R^{1'}$ is hydrogen C-alkylating the product to give a compound in which $R^1$ is lower alkyl. Reaction with ammonia gives a compound of formula (II) in which $R^7$ is hydrogen which, if desired, may be alkylated to give a compound in which $R^7$ is lower alkyl. The C-alkylation may be carried out with a lower alkyl halide in presence of a strong base. Examples of strong bases are given above.

In an alternative method for preparing the compounds of general formula (I) in which $R^7$ is hydrogen, lower alkyl or aryl(lower)alkyl a diol of general formula (IX)

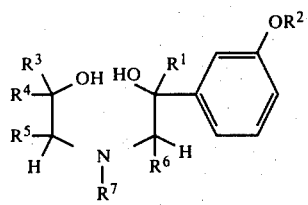 (IX)

wherein $R^1$, $R^2$, $R^3$, $R^4$, $R^5$, $R^6$ and $R^7$ are as defined above, is cyclodehydrated. Preferably $R^3$ and/or $R^4$ is hydrogen. The cyclodehydration may be effected under acidic conditions e.g. with hydrochloric, hydrobromic or sulphuric acid. Under certain conditions (e.g. refluxing with concentrated hydrobromic acid) a lower alkyl $R^2$ group in the diol (IX) may be cleaved to give a product (I) in which $R^2$ is hydrogen. The diol of general formula IX may be prepared by reacting an oxiran of general formula (VI) given above with a hydroxyamine of general formula (X)

If any of the processes described above the compound of the invention is obtained as an acid addition salt, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methane-sulphonic and p-toluenesulphonic acids.

The compounds of the invention possess one or more asymmetric carbon atoms and the compounds may be in the form of the pure enantiomorphs or mixtures of such enantiomorphs, such as racemates and diastereoisomers. If for example $R^3$ and $R^4$ are different but $R^5$ and $R^6$ are both hydrogen the compounds possess two asymmetric carbon atoms and mixtures of such diastereoisomers may be separated by chromatography (e.g. high pressure liquid chromatography) or fractional crystallisation. The ratio of the diastereoisomers in the mixture may be affected by the choice of reagent used in the cyclisation process to produce the starting materials or final compounds. Optical isomers may be prepared by resolving a racemic mixture by standard methods described in the literature. The racemate may be prepared by any of the processes outlined above. It is to be understood that the resolution may be carried out on the racemic mixture of the final desired product or it may be carried out on a racemic precursor of the desired compound provided further chemical reaction does not cause racemisation.

In any of the above processes the reaction conditions are chosen having regard to the reactivity and stability of the substituents, such that the desired product is obtained.

The novel compounds of the invention possess pharmacological activity, in particular analgesic activity and/or opiate antagonistic activity as indicated by standard pharmacological testing. For example one of the isomers of 2-ethyl-2-(3-hydroxyphenyl)-4,6-dimethylmorpholine ("isomer B" in Example 5 below), a representative compound of the invention produced analgesia in 10 rats out of 10 at a dosage of 25 mg/kg subsutaneously in a rat tail flick method (based upon D'Amour and Smith, J. Pharmacol., 1941, 72, 74). The same compound in a phenylbenzoquinone-induced writhing test (based upon E. Siegmund et al, Proc. Soc. exp. Biol. Med., 1957, 95, 729–731) had an $ED_{50}$ of 0.66 mg/kg subcutaneously. The compound has an $ED_{50}$ of 1.9 mg/kg subcutaneously in a procedure for opiate antagonistic activity based upon Aceto et al, Brit. J.Pharmac., 1969, 36, 225–239. Some of the compounds are useful as intermediates for other compounds of the invention by methods described above.

The invention provides a pharmaceutical composition comprising a compound of general formula (I) or a pharmaceutically acceptable salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, lactose, pectin, dextrin, starch, gelatin, tragacanth, methylcellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredients; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

The following Examples illustrate the invention.

EXAMPLE 1

2-Ethyl-2-(3-methoxyphenyl) oxiran

A solution of trimethylsulphoxonium iodide (88.3 g; 0.4 mole) in dry dimethylsulphoxide (500 ml) was slowly added to sodium hydride (9.6 g; 0.4 mole) in an atmosphere of nitrogen, with vigorous stirring, the temperature not being allowed to exceed 10° C. After two hours, evolution of hydrogen was essentially complete. Maintaining the temperature, the grey mixture was treated with suspension of 3-methoxypropiophenone (48 g; 0.293 mole) in dry dimethylsulphoxide (100 ml). The mixture was stirred at ambient temperature for 1½ hours, and then at 50° C. for 1 hour. The cooled mixture was treated with water (250 ml), and then shaken with two portions of ether (400 ml). The ether layers were washed with water and dried over magnesium sulphate, giving a residual 67 g of 90% pure epoxide title compound. Distillation gave 31 g of title compound bp (1 mm) 80°–86° C.

EXAMPLE 2

α-Ethyl-(3-methoxy)-α-[(methylamino)methyl]benzene methanol

2-Ethyl-2-(3-methoxyphenyl)oxiran (10.4 g) was heated with 33% ethanolic methylamine (50 ml) in a 300 ml bomb at 90° C. for 5 hours. The oil that remained after removal of solvent was dissolved in ether (200 ml) and acidified with ethereal hydrogen chloride. The white precipitate was crystallised twice from isopropyl alcohol to give the title compound as the hydrochloride (6.4 g; mp 180°–82° C.).

Analysis: Found: C,58.8; H, 8.5; N, 5.8%; $C_{12}H_{19}NO_2HCl$ requires C, 58.68; H, 8.2; N, 5.7%.

EXAMPLE 3

6-Ethyl-6-(3-methoxyphenyl)-2,4-dimethyl-3-morpholinone (a) A solution of α-ethyl-(3-methoxy)-α-[(methylamino) methyl]benzene methanol (20.9 g, 0.1 mole) and triethylamine (13.9 ml, 0.1 mole) in dry toluene (200 ml) was treated at 0°–5° C. with a solution of 2-bromopropionylbromide (21.6 g, 0.1 mole) in toluene (100 ml). The mixture was stirred for 1 hour at ambient temperature and then washed with 2 M hydrochloric acid (2×50 ml), with water (2×50 ml), and dried (MgSO$_4$). Removal of solvent left 33.0 of crude N-[2-hydroxy-2-(3-methoxyphenyl)butyl]-N-methyl-2-bromopropionamide.

(b) A solution of the bromoamide (33 g) in dry toluene (100 ml) was added to sodium hydride (7.2 g; 0.3 mole) in dry dimethylformamide (200 ml) such that the temperature did not exceed 10° C., in an atmosphere of nitrogen. After heating at 90° C. for 1½ hours the mixture was cooled and carefully poured on to 1500 ml of water. The toluene layer was separated, and the aqueous layer shaken with toluene (2×800 ml). The combined toluene layers were washed with water (2×1000 ml) and dried (MgSO$_4$). Removal of solvent left the title compound (24.1 g) as an orange oil. A small quantity was distilled to provide an analytical sample (bp 140°-7° C.; 0.35 mm). Chromatography showed that the product contained diastereoisimer A (apparently 2R*, 6R* configuration) and diastereoisomer B (apparently 2R*, 6S* configuration) in the ratio of about 2:1.

Analysis:
Found: C, 68.1; H, 8.3; N, 4.8%; C$_{15}$H$_{21}$NO$_3$ requires C, 68.4; H, 8.04; N, 5.32%.

(c) The crude bromamide from step (a) (91 g) in isopropyl alcohol (250 ml) was added dropwise to a stirred solution of sodium hydroxide (10 M 56 ml) in isopropyl alcohol (450 ml) between 10°-15° C. After about 1 h. at room temperature the isopropyl alcohol was removed under reduced pressure, the product diluted with water and extracted into ether. The organic extracts were washed with water and 2 M hydrochloric acid. After drying (MgSO$_4$) the solvent was removed to leave an oil which on distillation afforded 55.4 g, of a viscous colourless liquid b.p. (at 1 mbar) 162°-164° C. glc showed that the product contained 47% diastereoisomer A (apparently 2R*, 6R* configuration) 53% diastereoisomer B, (apparently 2R*, 6S* configuration).

EXAMPLE 4

2-Ethyl-2-(3-methoxyphenyl)-4,6-dimethylmorpholine

6-Ethyl-6-(3-methoxyphenyl)-2,4-dimethyl-3-morpholinone (4.5 g, 0.017 mole) in dry ether (100 ml) was added to a suspension of lithium aluminium hydride (3.0 g) in dry ether (100 ml) and the suspension refluxed for 6 hours. After stirring at ambient temperature overnight, the cooled mixture was treated with a solution of potassium sodium tartrate (40 g) in water (200 ml). The ether layer was combined with two 100 ml ether extracts from the aqueous layer. The ether layers were washed with water (50 ml) and dried (MgSO$_4$). Removal of solvent left a pale, pungent oil (3.5 g) containing a mixture of diastereoisomers. The isomers were separated by chromatography on silica eluting with ethyl acetate and the resulting bases were converted to their hydrochlorides:

Title compound hydrochloride (Isomer A, apparently of 2R*, 6R* configuration), m.p. 221°-222°.

Analysis: Found: C, 63.1; H, 8.7; N, 4.8%; C$_{15}$H$_{23}$NO$_2$·2HCl requires C, 63.1; H, 8.5; N, 4.9%.

Title compound hydrochloride (Isomer B, apparently of 2R*, 6S* configuration), m.p. 188°-190° C.

Analysis: Found: C, 62.9; H, 8.7; N, 4.9%: C$_{15}$H$_{23}$NO$_2$·HCl requires C, 63.1; H, 8.5; N, 4.9%.

EXAMPLE 5

2-Ethyl-2-(3-hydroxyphenyl)-4,6-dimethylmorpholine (a) Isomer A

2-Ethyl-2-(3-methoxyphenyl)-4,6-dimethylmorpholine (7.0 g) was refluxed for 2.5 hours with aqueous 48% hydrobromic acid (50 ml). After removal of the solvent under reduced pressure the residue was re-evaporated using isopropyl alcohol to remove last traces of HBr and water. Fractional crystallisation of the residue (10.5 g) from isopropyl alcohol/ether gave 1.53 g of 95% stereochemically pure title compound isomer A hydrobromide (m.p. 241°-5° C.).

Analysis: Found: C, 53.0; H, 7.2; N, 4.05%; C$_{14}$H$_{21}$NO$_2$·HBr requires: C, 53.2; H, 7.0; N, 4.4%.

NMR data indicate that Isomer A is apparently the (2R*, 6R*)-2-ethyl-2-(3-hydroxyphenyl)-4,6-dimethylmorpholine compound:

$^1$H NMR of the hydrobromide in MeOH-d$_4$ (60 MHz-Varian EM 360 instrument).

Signals are given as: chemical shift (δ in p.p.m. from tetramethylsilane internal standard), multiplicity (s-singlet, d-doublet, t-triplet, q-quartet, m-multiplet, dd-doublet of doublets, dt-doublet of triplets), coupling constants in Hz, assignment. 0.75, t, 7 Hz, CH$_3$CH$_2$-; 1.25, d, 6 Hz, 6 Me; 1.75, q, 7 Hz, CH$_3$CH$_2$-; 2.8, t, 12 Hz, H5 axial; 2.95, s, 4 Me; 3.1, d, 12 Hz, H3 axial; 3.2, d, 12 Hz, H5 equatorial; 3.9, m, H6 axial; 4.35, dd, 12 Hz and 2 Hz, H3 equatorial; 6.8-7.4, m, aromatic protons.

(b) Isomer B

A further 6.6 g of the methyl ether was demethylated as described above. The residue was crystallised from isopropyl alcohol (100 ml), to give 3.23 g of white crystals, that proved to be 88% isomer A. The mother liquor (containing 57% isomer B) was basified with 0.880 ammonia. The residue on evaporation was crystallised from 30 ml of acetonitrile (filtering hot) to give 1.17 g of the phenol as white crystals (91% isomer B). The phenol was converted to the hydrobromide in isopropyl alcohol (30 ml), and on cooling white crystals (0.9 g) of the title compound isomer B hydrobromide were precipitated (m.p. 222°-26° C.), 99% pure by GLC.

Analysis: Found: C, 53.5; H, 7.4; N, 4.4%; C$_{14}$H$_{21}$NO$_2$·HBr requires: C, 53.2; H, 7.0; N, 4.4%.

Melting point of the hydrochloride: 259°-261° (decomp) NMR data indicate that isomer B is apparently the (2R*, 6S*)-2-ethyl-2-(3-hydroxyphenyl)-4,6-dimethylmorpholine compound:

$^1$H NMR of the hydrochloride in MeOH-d$_4$ (60 MHz-Varian EM360 instrument).

0.6, t, 7 Hz, CH$_3$CH$_2$; 1.3, d, 6 Hz, 6 Me; 1.8, m, and 2.8, m, CH$_3$CH$_2$; 2.7, m, H5 axial; 2.8, m, H3 axial; 2.9, s, 4 Me; 3.45, dt, 12 Hz and 2 Hz, H5 equatorial; 3.8, dd, 12 Hz and 2 Hz, H3 equatorial; 4.2, m, H6 axial; 6.8-7.3, m, aromatic protons.

EXAMPLE 6

N-[2-Hydroxy-2-(3-methoxyphenylbutyl]-N-methyl-2-bromoacetamide

Bromoacetyl bromide (1.8 ml) was added dropwise to α-ethyl-(3-methoxy)-α-[(methylamino)methyl]benzene methanol (4.15 g) and triethylamine (2.76 ml) in methylene chloride (50 ml) at such a rate as to keep the temperature below 10° C. After stirring at ambient temperature for 30 minutes the solution was washed with 2 N HCl (20 ml) and water (20 ml) and dried over magnesium sulphate. Removal of the solvent left the crude title compound, which was used in Example 7 without further purification (6.4 g).

EXAMPLE 7

6-Ethyl-6-(3-methoxyphenyl)-4-methyl-3-morpholinone

The crude product from Example 6 (6.4 g. 0.02 mol.) in dry toluene (30 ml) was added dropwise to a suspension of sodium hydride (1.4 g, 0.058 mol.) in dry dimethylformamide (100 ml) at 5° C., and the mixture heated at 80° C. for 30 minutes. The cooled mixture was poured on to water (200 ml) and shaken with toluene (4×50 ml). The toluene layers were washed with water (2×100 ml) and dried over magnesium sulphate, giving the title compound (2.6 g.).

EXAMPLE 8

2-Ethyl-2-(3-methoxyphenyl)-4-methylmorpholine

6-Ethyl-6-(3-methoxyphenyl)-4-methyl-3-morpholinone (3.6 g) in dry ether (100 ml) was added to a suspension of lithium aluminium hydride (1.7 g) in ether (100 ml) and the suspension refluxed for 5 hours. The cooled mixture was treated with water (100 ml) containing potassium sodium tartrate (25 g). The ether layer was combined with two more ether extracts from the aqueous layer, and then washed with water and dried (MgSO4). The solvent was removed to leave an oil (3.6 g). This was dissolved in isopropyl alcohol (50 ml) and acidified with ethereal hydrogen chloride. On cooling white crystals of the title compound as the hydrochloride were obtained (2.38 g, m.p. 214°–215° C.).

Analysis: Found: C, 62.15; H, 8.22; N, 4.89%. $C_{14}H_{21}NO_2.HCl$ requires C, 61.87; H, 8.16; N, 5.15%.

EXAMPLE 9

2-Ethyl-2-(3-hydroxyphenyl)-4-methylmorpholine

2-Ethyl-2-(3-methoxyphenyl)-4-methylmorpholine (4.0 g, 0.015 mol) was refluxed for 2.5 hour with aqueous 48% hydrobromic acid (50 ml). The residue on evaporation was dissolved in 2 M sodium hydroxide (50 ml) and the non-phenolic material (about 1.0 g) extracted with ether. The aqueous layer was neutralised with solid ammonium chloride and the phenol extracted with ether/chloroform. The residue on removal of the solvents (1.3 g) was dissolved in isopropyl alcohol and treated with 40% aqueous HBr. The residue on evaporation crystallised from isopropyl alcohol as the hydrobromide hemi-isopropanolate of the title compound (1.24 g, m.p. 99°–104° C.).

Anaysis: Found: C, 52.0; H, 7.24; N, 3.8%; $C_{13}H_{19}NO_2.HBr \frac{1}{2}(C_3H_7OH)$ requires C, 52.41; H, 7.28; N, 4.2%.

EXAMPLE 10

2-(3-Methoxyphenyl)-2-methyloxiran

Trimethyloxosulphonium iodide (100 g, 0.45 mole) was added as a slurry in dimethylsulphoxide (100 ml) to a stirred cooled suspension of sodium hydride (22.6 g of a 50% dispersion of oil, washed free from oil with ether) under nitrogen, keeping the internal temperature at 20° C. by ice-cooling. After stirring at room temperature for 1 hour 3-methoxyacetophenone (45 g, 0.3 mole) was added in a 1:1 mixtures of dry tetrahydrofuran-dimethylsulphoxide (100 ml). The reaction mixture was slowly heated to 50° C. over 1 hour and this temperature was maintained for 1 hour. The mixture was cooled, poured on to ice water and extracted with ether (4×150 ml). The combined extracts were washed with brine, dried (MgSO4) and evaporated to an oil (34.0 g) and used crude for the preparation of (3-methoxy)-α-methyl-α[(methylamino)methyl]benzene methanol.

EXAMPLE 11

(3-Methoxy)-α-methyl-α-[(methylamino)methyl]benzene methanol 2-(3-Methoxyphenyl)-2-methyloxiran (34.0 g) was stirred with aqueous methylamine (100 ml, 33%) and alcoholic methylamine (200 ml, 33%) overnight at ambient temperature. The mixture was evaporated to an oil under reduced pressure, dissolved in hydrochloric acid (2 M) and extracted with toluene. After basifying the aqueous acid with sodium hydroxide (5 M) the basic oil was extracted with toluene and dried (MgSO4). The solvent was removed under reduced pressure to leave the title compound as an oil (27.7 g). The hydrochloride was formed in isopropyl alcohol-ethereal hydrogen chloride, m.p. 155°–156° C. (Found: C, 57.55; H, 8.3; N, 5.8% $C_{11}H_{17}NO_2HCl$ requires C, 57.0; H, 7.8; N, 6.0%.

EXAMPLE 12

6-(3-Methoxyphenyl)-2,4,6-trimethyl-3-morpholinone

2-Bromopropionylbromide (28.7 g, 0.13 mole) in dichloromethane (100 ml) was added dropwise with stirring to a solution of (3-methoxy)-2-methyl-2-[(methylamino)methyl]benzene methanol (25.9 g, 0.13 mol) and triethylamine (13.5 g) in dichloromethane (200 ml) keeping the temperature of the reaction between 10°–15° C. by ice-cooling. After 2 hours the reaction was washed with water, dilute hydrochloric acid and brine, dried (MgSO4) and evaporated to an oil (46.9 g). The last traces of dichloromethane were removed from the oil by evaporation with toluene. The oil was dissolved in dry toluene (200 ml) and added dropwise to a stirred suspension of sodium hydride (9.6 g, 0.2 mole of a 50% dispersion in oil pre-washed with ether) in dry dimethylformamide (200 ml) under nitrogen. The exothermic reaction which took place was kept at 35° C. by adjusting the rate of addition. When the addition was completed the reaction mixture was heated to 85° C. for 20 min. The reaction mixture was cooled and cautiously added to ice water (300 ml). The mixture was extracted with toluene and the organic extracts washed with dilute hydrochloric acid then brine. After drying (MgSO4) the solvent was removed to leave an oil which was distilled affording the title compound (25.8 g) as a colourless oil, bp 148°–149° at 0.7 mbar. Glc showed that the product was a mixture of diastereoisomers containing isomer A (apparently 2R*6R* configuration) 65% and isomer B (apparently 2R*6S* configuration) 35% by glc.

EXAMPLE 13

2-(3-methoxyphenyl)-2,4,6-trimethylmorpholine

The above mixture of isomers of 6-(3-methoxyphenyl)-2,4,6-trimethyl-3-morpholinone (15.8 g) in dry ether (50 ml) was added dropwise to a stirred suspension of lithium aluminium hydride (4.0 g) in ether (250 ml). After heating under reflux for 3 hours the reaction mixture was cooled and the complex decomposed by the cautious, successive addition of water (4 ml), 2 M sodium hydroxide (8 ml) and anhydrous MgSO4. The inorganic material was filtered off and the filtrate removed under reduced pressure affording 15 g of oil.

The diastereoisomers were separated on a column of Woelm silica activity 1, eluting with ethylacetate giving the isomer A (apparently 2R* 6R* configuration) (8.95 g) and the isomer B (apparently 2R* 6S* configuration) (4.67 g).

The two diastereoisomers were converted to their crystalline hydrochlorides for characterisation.

Isomer A (apparently 2R*6R* configuration) mp 215°–218° C. Found: C, 61.3; H, 8.2; N, 5.2%.

Isomer B (apparently 2R*6S* configuration) mp 238°–239° C. Found: C, 61.9; H, 8.4; N, 5.1% $C_{14}H_{21}NO_2HCl$ requires C, 61.9; H, 8.2; N, 5.15%.

EXAMPLE 14

(a) 2-(3-Hydroxyphenyl)-2,4,6-trimethylmorpholine (Isomer A)

2-(3-methoxyphenyl)-2,4,6-trimethylmorpholine (Isomer A) (2.03 g) was heated under reflux with redistilled constant boiling hydrobromic acid (15 ml). After cooling and diluting with water the reaction was basified with conc. aqueous ammonia to give an oil which solidified affording 1.34 g of granular solid. The solid was recrystallised from toluene/light petroleum (bp 60°–80°) affording 1.03 g of feathery needles mp 150°–151° C. (Found: C, 70.9; H, 8.6; N, 6.2. $C_{13}H_{19}NO_2$ requires C, 70.55; H, 8.65; N, 6.3%). NMR data indicate that the product apparently has the (2R*,6R*)-configuration.

(b) 2-(3-Hydroxyphenyl)-2,4,6-trimethylmorpholine (Isomer B)

2-(3-methoxyphenyl)-2,4,6-trimethylmorpholine hydrochloride (Isomer B) (2.49 g) was heated under reflux with redistilled constant boiling hydrobromic acid (20 ml) under nitrogen for 1 hour. After cooling and diluting with water to 40 ml the mixture was basified with conc. aqueous ammonia. The oil which precipitated was extracted with dichloromethane. After drying (MgSO4) the solvent was removed affording a colourless oil which gave 1.16 g of colourless rhombs mp 142°–143° C. from toluene. (Found: C, 70.6; H, 8.7; N, 6.05%. $C_{13}H_{19}NO_2$ requires C, 70.55; H, 8.65; N, 6.3%. NMR data indicate that the product apparently has (2R*, 6S*)-configuration.

EXAMPLE 15

α-Ethyl-α-[N-(2-hydroxypropyl)aminomethyl]-3-methoxybenzene methanol

2-Ethyl-2-(3-methoxyphenyl)oxiran (14 g, 0.079 mole) and 1-amino-2-propanol (100 g., 1.33 mole) wee refluxed with ethanol (50 ml) for 12 hours. The solvent and excess aminopropanol was removed under reduced pressure. The residue was dissolved in methanol (80 ml) and acidified with ethereal hydrogen chloride. The methanol was evaporated and the residue taken up in water (250 ml). Non-basic material was extracted by shaking the aqueous solution with three portions of 100 ml of ether. The aqueous layer was neutralised with a large excess of 0.880 ammonia, and reextracted with ether (3×100 ml). The ether layers were washed with water and dried (MgSO4). Removal of solvent left the title compound in 98% purity (12.3 g).

EXAMPLE 16

2-Ethyl-2-(3-methoxyphenyl)-6-methylmorpholine

METHOD A The product from Example 15 (1.77 g, 0.007 mole) was treated dropwise at 0° C. with concentrated sulphuric acid (2.3 ml). The resulting green gum was allowed to stand overnight at room temperature and was then treated with 25 ml of crushed ice and after thorough mixing, 50 ml of water. The solution was neutralised with excess ammonia and the solution shaken with ether (2×50 ml). The ether layers were washed, and dried (MgSO4) and evaporated to give 360 mg of the title compound as a 50:50 mixture of diastereoisomers.

METHOD B (a) 2-Ethyl-2-(3-methoxyphenyl)oxiran (25 g, 0.14 mol) in ethanol (50 ml.) was heated with 0.880 ammonia (60 ml.) in a 300 ml. bomb at 90° C. for 16 hours. The residue on evaporation was dissolved in methanol and acidified with concentrated hydrochloric acid. The methanol was evaporated and the residue dissolved in 2 M hydrochloric acid (300 ml.) and shaken with toluene (2×200 ml). The aqueous layer was basified to pH=14 with 5 M sodium hydroxide and the amine extracted back into toluene (2×200 ml). The toluene layers were dried (MgSO4) and evaporated to give a light brown oil. This was dissolved in isopropyl alcohol (100 ml.) and acidified with ethereal hydrogen chloride. On cooling, white crystals of α-(aminomethyl)-α-ethyl-(3-methoxy)benzene methanol hydrochloride were precipitated (11.5 g, mp 160°–65° C.).

Analysis: Found: C, 57.8; H, 8.2; N, 5.0%. $C_{11}H_{17}NO_2HCl$ requires C, 57.02; H, 7.83; N, 6.04%.

(b) A solution of α-aminomethyl-α-ethyl-(3-methoxy)benzene methanol (15 g, 0.077 mol) and triethylamine (10.8 ml) in dichloromethane (100 ml) at 0° C. was treated slowly with 2-bromopropionyl bromide (8.12 ml, 0.077 mol) over 30 min. After a further 2 h the cooled mixture was treated with water (100 ml). The dichloromethane layer was washed with 5 M hydrochloric acid (100 ml) and water, and dried over magnesium sulphate. The residue containing N-[2-hydroxy-2-(3-methoxyphenyl)butyl]-2-bromopropionamide (22.8 g) was used without further purification.

(c) A solution of N-[2-hydroxy-2-(3-methoxyphenyl)-butyl]-2-bromopropionamide (22.6 g) in dry dimethylformamide (50 ml) was added slowly to a suspension of sodium hydride (6.7 g) in DMF (130 ml) at 8° C. The mixture was heated at 90° C. for 2 h under nitrogen. The cooled suspension was treated with water (200 ml) and shaken with toluene (2×100 ml). The toluene layers were washed with water and dried over magnesium sulphate giving an oil (15.8 g) that crystallised from ether.

The crude 6-ethyl-6-(3-methoxyphenyl)-2-methyl-3-morpholinone was added in ether to a cooled suspension of lithium aluminium hydride (12 g) in ether and then refluxed for 6 h. A solution of potassium sodium tartrate (132 g) in water (300 ml) was slowly added to the cooled suspension. The ether layer was washed and dried giving the title compound as a yellow oil (12.3 g). Both this and the parent morpholinone were mixtures of equal proportions of diastereoisomers in >95% purity.

EXAMPLE 17

2-Ethyl-2-(3-hydroxyphenyl)-6-methylmorpholine

2-Ethyl-2-(3-methoxyphenyl)-6-methylmorpholine (2.63 g) was refluxed with aq 48% HBr (20 ml) for 2.5 h. The residue on evaporation was re-evaporated from isopropyl alcohol several times, giving ultimately a green gum (2.8 g), which was dissolved in methanol and basified with 0.880 ammonia. The methanol and ammonia were evaporated under reduced pressure and the aqueous remaining was shaken with chloroform (2×100 ml). The chloroform layers were washed and dried and evaporated, leaving an orange oil (8.4 g) that crystallised from ethyl acetate (25 ml). The yellow hygroscopic solid was dissolved in isopropyl alcohol (15 ml) and acidified with ethereal hydrogen chloride. On cooling crystals of the title compound hydrochloride were obtained (0.85 g, mp 200°–205° C.). Gas-liquid chromatography revealed the isomer ratio to be 20:1.

The free base was crystallised from acetonitrile giving an analytical sample.

Analysis: Found: C, 70.0; H, 9.0; N, 5.9% $C_{13}H_{19}NO_2$ requires C, 70.55; H, 8.65; N, 6.33%.

EXAMPLE 18

6-(3-Methoxyphenyl)-2,2,4,6-tetramethylmorpholine 6-(3-Methoxyphenyl)-2,4,6-trimethyl-3-morpholinone (4.9 g, 0.02 mol) in dry tetrahydrofuran (100 ml) was added dropwise with stirring to lithium diisopropylamide (0.04 mol) in THF/hexane 1:1 (75 ml). After stirring at room temperature for 20 mins iodomethane (5.6 g 0.04 mol) was added dropwise. After stirring at room temperature for 2 h a further portion of iodomethane (1 ml) was added and the reaction stirred overnight. The reaction mixture was decomposed by addition to a mixture of ice and hydrochloric acid, the organic layer was separated and the aqueous extracted with ether. After drying ($MgSO_4$) the solvent was removed under reduced pressure to leave 5.6 g of colourless oil of 6-(3-methoxyphenyl)-2,2,4,6-tetramethyl-3-morpholone.

The crude product was dissolved in ether (50 ml) and added dropwise to lithium aluminium hydride (2 g) in ether (100 ml). After stirring at room temperature for 2 h the reaction mixture was decomposed by the addition of water (2 ml) and 2 M sodium hydroxide (4 ml.) The suspension was filtered and the basic material isolated in ether. After drying ($MgSO_4$) the solvent was removed to leave the title compound as an oil which was converted to its hydrochloride salt (2.4 g) mp 218°–220°.

Analysis: Found C, 63.6; H, 8.9; N, 4.8%; $C_{15}H_{23}NO_2HCl$ requires C, 63.0; H, 8.5; N 4.9%.

EXAMPLE 19

2-(3-Hydroxyphenyl)-2,4,6,6-tetramethylmorpholine 6-(3-Methoxyphenyl)-2,2,4,6-tetramethylmorpholine hydrochloride (1.4 g) was heated under reflux with concentrated hydrobromic acid (20 ml) under nitrogen for 3 h. The dark solution was reduced to small volume under reduced pressure, diluted with water and neutralised with ammonium hydroxide. The product was extracted into dichloromethane, dried over magnesium sulphate and evaporated to an oil which crystallised from toluene. The title base was converted to its hydrobromide salt by treatment in isopropyl alcohol with a solution of hydrogen bromide in dry ether affording the title compound as its hydrobromide (600 mg) mp 216°–217° C.

Analysis: Found C, 53.2; H, 7.05; N, 4.3%; $C_{14}H_{21}NO_2HBr$ requires C, 53.2; H, 7.0; N, 4.4%.

EXAMPLE 20

2-Ethyl-2-(3-methoxyphenyl)-4,6,6-trimethylmorpholine

6-Ethyl-6-(3-methoxyphenyl)-2,4-dimethyl-3-morpholinone (6.6 g, 0.03 mol) in dry tetrahydrofuran (20 ml) was added to a cooled stirred solution of lithium diisopropylamide (0.06 mol) in THF/hexane 1:1 (70 ml) under nitrogen. The mixture was stirred for 1 h at room temperature and iodomethane (8.5 g) was added. The reaction was stirred overnight at room temperature then poured on to a mixture of ice and concentrated hydrochloric acid. The oil was extracted with dichloromethane, washed with water dried ($MgSO_4$) and evaporated to an oil [6-ethyl-6-(3-methoxyphenyl)-2,2,4-trimethyl-3-morpholinone] (6.8 g).

The above oil in dry ether (50 ml) was added dropwise to a stirred suspension of lithium aluminium hydride (3 g) in ether (150 ml). After stirring at room temperature for 2 h the reaction mixture was decomposed by the addition of water (2 ml) and 4 M sodium hydroxide solution (4 ml). After the addition of magnesium sulphate the reaction mixture was filtered and the filtrate evaporated to a colourless oil (6.5 g). The oil was dissolved in isopropyl alcohol and a solution of hydrogen chloride in dry ether added to give the title compound as the hydrochloride (5.88 g), fine white needles mp 208°–10° C.

Analysis: Found C, 63.7; H, 8.8, N 4.7%; $C_{16}H_{25}NO_2HCl$ requires C, 64.1; H, 8.7; N, 4.7%.

EXAMPLE 21

2-Ethyl-2-(3-hydroxyphenyl)-4,6,6-trimethylmorpholine

2-Ethyl-2-(3-methoxyphenyl)-4,6,6-trimethylmorpholine hydrochloride (1 g) was heated under $N_2$ and under reflux with stirring with a solution of diisobutyl aluminium hydride (15 ml of a 25% w/w solution in toluene) for 24 h. The reaction mixture was cooled, and decomposed by the cautious addition of a saturated solution of potassium sodium tartrate. The toluene layer was separated and the aqueous phase reextracted with toluene. After the combined organic extracts were washed with saturated sodium chloride solution they were dried ($MgSO_4$) and evaporated to an oil which gave 742 mg of crystalline title compound hydrochloride salt mp 185°–188° C. from isopropyl alcohol and a solution of hydrogen chloride in dry ether.

Analysis: Found: C, 63.0; H, 8.5; N 4.9%; $C_{15}H_{23}NO_2HCl$ requires C, 63.15; H, 8.5; N, 4.9%.

EXAMPLE 22

2-Ethyl-2-(3-methoxyphenyl)-4-methyl-6-phenylmorpholine

2-Chlorophenylacetylchloride (4.73 g, 0.025 mole) in dichloromethane (20 ml) was added with stirring and cooling to a solution of α-ethyl-3-methoxy-α-[(methylamino)methyl] benzene methanol (5.35 g, 0.025 mol) and triethylamine (2.53 g, 0.025 mol) in dichloromethane (50 ml). After stirring at room temperature for 2 h the reaction mixture was washed with water and dilute hydrochloric acid, dried ($MgSO_4$) and the solvent removed under reduced pressure affording the chloroamide as a dark oil (8.9 g).

The crude chloroamide (8.9 g) in isopropyl alcohol (20 ml) was added dropwise with stirring to a solution of sodium hydroxide (10 M 6 ml) in isopropyl alcohol (20 ml) at room temperature. After 1 h the isopropyl alcohol was removed under reduced pressure, and the resulting oil extracted into dichloromethane. After washing with water and 2 M hydrochloric acid the organic phase was dried (MgSO$_4$) and evaporated affording 6.2 g of 6-ethyl-6-(3-methoxyphenyl)-4-methyl-2-phenyl-3-morpholinone as an oil shown to be a mixture of two diastereoisomers 60:40 by glc.

The crude oil in ether was added to a suspension of lithium aluminium hydride (3.0 g) in ether and stirred at room temperature for 2 h. Water (3 ml) and 10 M sodium hydroxide (3 ml) was then added, the precipitate was filtered and washed with ether. After drying (MgSO$_4$) the solvent was removed to leave an oil (6.0 g) which was chromatographed on silica eluting with ethylacetate/light petroleum (2:1).

The first diastereoisomer (Isomer A) to be eluted from the column was the title compound of apparently 2R*, 6R* configuration and it was converted to its hydrochloride salt 2.34 g, m.p. 185°–188° C.

Analysis: Found C, 69.4; H, 7.5; N 4.1%; $C_{20}H_{25}NO_2HCl$ requires C, 69.05; H, 7.5; N 4.0%.

The second product (Isomer B) eluted was the title compound of apparently 2R*, 6S* configuration and it was converted to its hydrochloride salt, (830 mg) mp 195°–196° C.

Analysis: Found C, 69.3; H, 7.6; N 3.9%; $C_{20}H_{25}NO_2HCl$ requires C 69.05; H, 7.5; N 4.0%.

EXAMPLE 23

2-Ethyl-2-(3-hydroxyphenyl)-4-methyl-6-phenylmorpholine (A) 2-Ethyl-2-(3-methoxyphenyl)-4-methyl-6-phenyl-morpholine hydrochloride (isomer A from Example 22) (1.0 g) was heated under reflux with concentrated hydrobromic acid (10 ml). After 1 h crystals of product were deposited. After cooling the product was filtered and washed with water. The product was recrystallised from ethanol—ether affording the title compound apparently of 2R*, 6R* configuration (660 mg), mp 225°–256° C.

Analysis: Found C 60.3; H, 6.5; N, 3.9%; $C_{19}H_{23}NO_2$ HBr requires C, 60.3; H, 6.4; N 3.7%.

(B) 2-Ethyl-2-(3-methoxyphenyl)-4-methyl-6-phenyl-morpholine hydrochloride (Isomer B from Example 22) (607 mg) was heated under reflux with concentrated hydrobromic acid (5 ml) for 1.25 h. On cooling crystals and a dark gum separated. The hydrobromic acid was removed under reduced pressure and the gummy product re-evaporated with portions of isopropyl alcohol. The product was recrystallised from isopropyl alcohol to give the title compound of apparently 2R*,6S* configuration (422 mg), mp 250°–252° C.

Analysis: Found C, 60.5; H, 6.5; N, 3.3%; $C_{19}H_{23}NO_2$ HBr requires C, 60.3; H, 6.4; N, 3.7%.

EXAMPLE 24

2-(3-Methoxyphenyl)-2,4-dimethylmorpholine

The title compound was prepared by a process analogous to that of Examples 12 and 13 employing bromoacetyl bromide (following the procedure of Example 6) in place of 2-bromopropionylbromide. The title compound was obtained as the hydrochloride mp 245°–247° (decomp.)

Analysis: Found: C, 60.6; H, 8.0; N, 5.3%; $C_{13}H_{19}NO_2HCl$ requires C, 60.5; H, 7.8; N, 5.4%.

EXAMPLE 25

2-(3-Hydroxyphenyl)-2,4,-dimethylmorpholine

The title compound was obtained as the hydrochloride quarter hydrate, mp 204°–206° following a procedure analogous to that of Example 9.

Analysis: Found: C, 58.2; H, 7.5; N, 5.5%; $C_{12}H_{17}NO_2HCl.\frac{1}{4}H_2O$ requires: C, 58.1; H, 7.5; N 5.6%.

EXAMPLE 26

2-Ethyl-2-(3-methoxyphenyl-6-methylmorpholine

2-Ethyl-2-(3-hydroxyphenyl)-4,6-dimethylmorpholine (Isomer A of Example 4) (1.24 g) in 1,2-dichloroethane (10 ml) was treated with vinyl chloroformate (0.6 ml) at room temperature. After 5 min. a colourless precipitate had formed. The mixture was heated to reflux for 1 h. The mixture was then evaporated under reduced pressure, leaving an oil which crystallised on standing to a grey-brown solid (1.54 g).

This solid was dissolved in toluene (75 ml) and filtered. The filtrate was evaporated, leaving a pale brown oil which slowly crystallised (1.34 g). This material was recrystallised from cyclohexane (3 ml) giving 2-ethyl-2-(3-methoxyphenyl)-6-methyl-4-vinyloxycarbonylmorpholine (apparently of 2R*, 6R* configuration) as colourless crystals (0.87 g) mp 86°–88°.

Found: C, 66.7; H, 7.5; N, 4.4; $C_{17}H_{23}NO_4$ requires: C, 66.9; H, 7.6; N, 4.6%.

The above 4-vinyloxycarbonylmorpholine was dissolved in absolute ethanol (5 ml) containing 6 M ethereal hydrogen chloride (1 ml). The mixture was heated to reflux for 2 h. Further 6 M ethereal hydrogen chloride (1 ml) was added and the mixture was heated to reflux for a further 1 H, when TLC showed complete conversion to a single more polar, basic product. The solvent was removed and the residue was re-evaporated with carbon tetrachloride (2×10 ml). The residual oil was triturated with ethyl acetate-ether to give a colourless solid which was recrystallised from ethyl acetate—80°–100° petrol-methanol (trace) giving 2-ethyl-2-(3-methoxyphenyl)-6-methyl morpoline hydrochloride, (apparently of 2R*, 6R* configuration), as a colourless solid (0.55 g), mp 130°–132°.

Found: C, 62.2; H, 8.2; N, 4.7; $C_{14}H_2NO_2HCl$ requires C, 61.9; H, 8.2; N, 5.15%.

EXAMPLE 27

2-Ethyl-2-(3-hydroxyphenyl)-6-methylmorpholine

2-Ethyl-2-(3-hydroxyphenyl)-4,6-dimethylmorpholine (Isomer A Example 4) (4.55 g), 2,2,2-trichloroethyl chloroformate (3.0 ml 4.62 g) and potassium carbonate (2.75 g) were heated together under reflux in 1,2-dichloroethane (175 ml) for 60 h. The cooled solution was extracted with 2 M hydrochloric acid (3×100 ml) and then with saturated brine (50 ml). The combined aqueous phases were back extracted once with ether (100 ml) and the combined organic phases were dried (Na$_2$SO$_4$) and evaporated, leaving the crude urethane as a brown oil (7.1 g).

The crude urethane (7.1 g) was stirred with zinc dust (7.1 g) in 9:1 v/v acetic acid-water for 4½ hr. at room temperature. The excess of zinc was removed by filtration and washed with glacial acetic acid (25 ml). The combined filtrate and washings were evaporated under reduced pressure to ~10 ml and the residue was diluted with water (25 ml) and made basic with 0.880 ammonia.

The precipitated product was extracted into ether (4×50 ml) dried (Na$_2$SO$_4$) and evaporated leaving crude 2-ethyl-2-(3-methoxyphenyl)-6-methylmorpholine (apparently of 2R*, 6R* configuration) as a clear brown oil (3.19 g).

The above crude oil (2.75 g) in toluene (50 ml) was treated under nitrogen with di-isobutylaluminium hydride (DIBAL-H) (25 ml/% in toluene, 48 ml) and the mixture was heated to reflux for 20 h. TLC indicated 30% reaction after this time. Further DIBAL-H (1 M in hexane, 105 ml) was added and the hexane solvent was distilled out under nitrogen (3 h) until toluene distilled. The residue was then refluxed for a further 38 h. The mixture was cooled and stored overnight under nitrogen, and was then cooled in dry ice-acetone. Methanol (8.5 ml) was added carefully dropwise resulting in vigorous evolution of hydrogen and heat. When the reaction subsided saturated Rochelle salt solution (∼3 ml) was added dropwise. The mixture was then allowed to warm slowly from −78° to 0° and further Rochelle salt solution (100 ml) was added. An exothermic decomposition again occurred and was controlled by replacing the −78° bath. On re-warming, the exothermic reaction was less vigorous and ultimately subsided. Further Rochelle salt solution (300 ml), ether (200 ml) and toluene (100 ml) were added and the mixture was stirred for ¾ hr. The phases then separated easily. The pH of the aqueous phase was brought to ∼8.5. The aqueous phase was extracted with ether (4×100 ml). The combined organic phases were dried (Na$_2$SO$_4$) and evaporated, giving a pink gum (2.86 g) which crystallised on seeding and trituration with a little acetonitrile to give the title compound as a pink solid, mp 75°–105°.

The solid was converted to its hydrochloride to give the title compound hydrochloride (apparently of 2R*, 6R* configuration) as pinkish crystals (1.91 g).

Analysis: Found: C, 60.4; H, 7.7; N, 5.4; C$_{13}$H$_{19}$NO$_2$HCl requires C, 60.6; H, 7.8; N, 5.4%.

EXAMPLE 28

4-Cyclopropylmethyl-2-ethyl-2-(3-methoxyphenyl)-6-methylmorpholine

2-Ethyl-2-(3-hydroxyphenyl)-6-methylmorpholine (product of Example 27) (1.3 g) was suspended in dichloromethane (20 ml) and triethylamine (1.7 ml) was added. Cyclopropanecarbonyl chloride (0.54 ml, 0.63 g) was added dropwise, causing an appreciable exotherm. The mixture was sealed and allowed to cool spontaneously. After 2 min. the product started to crystallise, and the solid was collected after 5 h and washed with dichloromethane (2×10 ml). IR indicated the solid to contain triethylamine hydrochloride, so it was dissolved in chloroform (200 ml) and washed with 2 M HCl (25 ml), water (50 ml and saturated sodium chloride solution (25 ml), and dried (Na$_2$SO$_4$). Removal of the solvent gave a colourless solid (0.79 g, A).

The dichloromethane filtrate and washings were diluted to 70 ml and washed with 2 M hydrochloric acid (2×25 ml), dried (Na$_2$SO$_4$) and evaporated, leaving a solid (0.68 g,B). Solids (A) and (B) were combined and recrystallised from methanol giving 4-cyclopropanecarbonyl-2-ethyl-2-(3-hydroxyphenyl)-6-methylmorpholine hemimethanolate (apparently of 2R*, 6R* configuration) as colourless crystals (0.65 g) mp 228°–9°.

Found: C, 69.6; H, 8.0; N, 4.1; C$_{17}$H$_{23}$NO$_3$.½CH$_3$OH requires C, 69.5; H, 8.25 N, 4.6%.

The above 4-cyclopropanecarbonylmorpholine (0.73 g) and lithium aluminium hydride (0.25 g) were heated together to reflux in dry tetrahydrofuran (50 ml) for 4.5 h. The cooled mixture was treated with saturated sodium potassium tartrate solution (50 ml), stirred until the aluminium salts dissolved, buffered to pH 7.8 with saturated ammonium chloride solution (50 ml) and the organic phase was separated. The aqueous phase was extracted with ether (3×50 ml) and the combined organic phases were dried (Na$_2$SO$_4$) and evaporated, leaving an oil containing traces of water. The oil was reevaporated with toluene (100 ml) and ethanol (20 ml) mixture, leaving a clear pale brown oil (0.77 g). This oil was taken up in ethyl acetate (5 ml) and added to a solution of toluene-p-sulphonic acid monohydrate (0.48 g) in warm ethyl acetate (15 ml). A crystalline solid formed almost immediately and was collected, washed with ethyl acetate (10 ml) and ether (10 ml), and dried, giving 4-cyclopropylmethyl-2-ethyl-2-(3-methoxyphenyl)-6-methylmorpholine toluene-p-sulphonate salt (apparently of 2R*, 6R* configuration) as fine colourless felted needles (0.96 g).

Found: C, 64.9; H, 7.6; N, 2.7; C$_{17}$H$_{25}$NO$_2$C$_7$H$_8$O$_3$S requires C, 6.44; H, 7.4; N, 3.1%.

EXAMPLE 29

2,6-Diethyl-2-(3-methoxyphenyl)-4-methylmorpholine 2,6-Diethyl-6-(3-methoxyphenyl)-4-methyl-3-morpholine, prepared by a process analogous to that of Example 3 (a) and (c) using 2-bromobutanoylchloride instead of 2-bromopropionylbromide, was reduced with lithium aluminium hydride, by a process analogous to that of Example 4 to give the title compound as the hydrochlorides:

Isomer A hydrochloride (apparently 2R*,6R*configuration) m.p. 190.5°–191.5°.

Found: C, 64.7; H, 8.8; N, 4.95%; C$_{16}$H$_{25}$NO$_2$HCl requires C, 64.1; H, 8.7; N, 4.7%

Isomer B hydrochloride (apparently 2R*, 6S* configuration), m.p. 219°–222°

Found: C, 6.40; H, 9.0; N, 4.9%; C$_{16}$H$_{26}$NO$_2$HCl requires C, 6.41; H, 8.7; N, 4.7%.

EXAMPLE 30

2,6-Diethyl-2-(3-hydroxyphenyl)-4-methylmorpholine

The hydrochloride salts of Example 29 were reacted with hydrobromic acid by a procedure analogous to that of Example 5 to give the title compound as the hydrochlorides:

Isomer A hydrochloride (apparently 2R*, 6R* configuration) m.p. 249°–252° (decomp with sublimation from 240°).

Found: C, 63.9; H, 8.8; N, 4.9%:

Isomer B hydrochloride (apparently 2R*, 6S* configuration) m.p. 265°–267° C. (decomp. with sublimation from 262°)

Found: C, 63.0; H, 8.5; N, 4.7%; C$_{15}$H$_{23}$NO$_2$HCl requires C, 63.0; H, 8.5; N, 4.9%.

EXAMPLE 31

2-(3-Hydroxyphenyl)-4,6-dimethyl-2-propylmorpholine

Following the method of Example 1,2-(3-methoxyphenyl)-2-propyloxiran was prepared from trimethylsulphoxonium iodide, 3-methoxybutyrophenone and sodium hydride. The oxiran was treated with 33% ethanolic methylamine affording 3-methoxy-α-[(methylamino)methyl]-α-propylbenzenemethanol isolated as the hydrochloride salt m.p. 168°–70° C.

Analysis: Found C, 60.6; H, 8.8; N, 5.4%; $C_{13}H_{21}NO_2HCl$ requires C, 60.0; H, 8.5; N, 5.4%.

2-bromopropionyl bromide (12.0 g) in dichloromethane (100 ml) was added to the above hydrochloride (14 g) in dichloromethane (100 ml) and triethylamine (11.12 g). After 2 h at room temperature the reaction was washed with dilute hydrochloric acid and water, dried ($MgSO_4$) and evaporated to an oil (19.3).

The oil was dissolved in isopropylalcohol (50 ml) and added dropwise to a stirred solution of sodium hydroxide (10 M, 15 ml) and isopropylalcohol (80 ml). After 2 h at room temperature the reaction was neutralised with concentrated hydrochloric acid, the alcohol removed under reduced pressure the resulting oil diluted with water and extracted into toluene. The toluene extracts were dried ($MgSO_4$) and evaporated to an oil giving 6-(3-methoxyphenyl)-2,4-dimethyl-6-propyl-3-morpholinone, (14.5 g). as a mixture of diastereoisomers.

After reducing with lithium aluminium hydride the 2-(3-methoxyphenyl)-4,6-dimethyl-2-propyl morpholine was obtained, the isomer ratio in this case was 45% corresponding to isomer A and 55% corresponding to isomer B. Diastereoisomers were separated on silica.

Treatment of each of the isomers with either refluxing hydrobromic acid or diisobutylaluminiumhydride in toluene gives the two stereoisomers of the title compound.

We claim:

1. A method of treating a mammal in need of an analgesic or opiate antagonist which comprises administering to said mammal an analgesically or opiate antagonistically effective amount of a compound selected from the group consisting of a morpholine derivative of the formula:

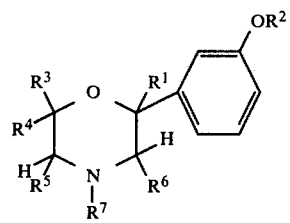

and a pharmaceutically acceptable acid addition salt thereof, wherein $R^1$ represents lower alkyl; $R^2$ represents hydrogen, lower alkyl, benzyl, loweralkoxymethyl or an acyl group; $R^3$ represents hydrogen, lower alkyl or phenyl; $R^4$, $R^5$ and $R^6$ are independently hydrogen or lower alkyl and $R^7$ is hydrogen, lower alkyl, lower alkenyl, lower alkynyl, aryl(lower)alkyl, tetrahydrofurylmethyl or cycloalkylmethyl, with the proviso that $R^2$ may only be lower alkyl when $R^7$ is other than hydrogen or lower alkyl.

* * * * *